United States Patent
Kirby et al.

[11] Patent Number: 6,134,295
[45] Date of Patent: Oct. 17, 2000

[54] APPARATUS USING A X-RAY SOURCE FOR RADIATION THERAPY PORT VERIFICATION

[75] Inventors: Thomas H. Kirby; Donna Siergiej; Edl Schamiloglu, all of Albuquerque, N. Mex.

[73] Assignee: University of New Mexico, Albuquerque, N. Mex.

[21] Appl. No.: 09/181,861

[22] Filed: Oct. 29, 1998

[51] Int. Cl.[7] .................................................. H01J 35/00
[52] U.S. Cl. ............................................. 378/65; 378/121
[58] Field of Search ........................................ 378/65, 121

[56] References Cited

U.S. PATENT DOCUMENTS 5,165,093  11/1992  Miller et al. .
5,471,516  11/1995  Nunan .
5,737,384   4/1998  Fenn .

*Primary Examiner*—Craig E. Church
*Attorney, Agent, or Firm*—Jagtiani & Associates

[57] ABSTRACT

An apparatus dedicated to taking diagnostic quality images to confirm the accuracy of radiotherapy treatments. The apparatus is sufficiently compact to be used in the existing treatment heads of linear accelerators capable of delivering both electron and x-ray radiation. A compact electron drift tube is made long enough to penetrate the substantial shielding of a linear accelerator, thereby obviating the need to locate the entire generating device within the head of the machine. The diameter of the drift tube of the present invention is made small enough to penetrate the shielding without causing undue leakage of radiation.

6 Claims, 2 Drawing Sheets

APPARATUS USING A X-RAY SOURCE FOR RADIATION THERAPY PORT VERIFICATION

BACKGROUND OF THE INVENTION

1. Field of the Invention

The present invention relates to an apparatus for applying an x-ray source, for radiation therapy port verification. More particularly, the present invention relates to an apparatus for taking high quality images of radiotherapy treatments to confirm the accuracy of those treatments.

2. Description of the Prior Art

U.S. Pat. No. 5,165,093 (Miller et al), assigned to The Titan Corporation, discloses an interstitial X-ray needle which is intended to deliver radiation and to treat tumors. One end of an elongated X-ray tube is coupled to an electron emitter and a converter element is disposed at the tip of the other end of the tube to convert electrons into X-rays. A solenoid coil is wound around the tube to provide a magnetic field to confine the electrons within a narrow beam. The tube and the coil are encased in an elongated outer casing, and a pipe is coaxially disposed between the casing and the tube thereby defining an inner annular flow chamber between the tip of the tube and the coolant inlet in the casing and an outer annular flow chamber between the tip of the tube and a coolant outlet in the casing.

The x-ray needle according to Miller et al has a diameter small enough so that it can be inserted into a patient without causing significant damage to the tissue between the skin and the tumor site, an increasing the applicability of x-ray therapy for the treatment of cancerous internal body parts. By winding the solenoid coil around the beam transport tube and thereby providing a magnetic field that tightly confines the emitted electrons, electron loss and stray x-radiation is prevented. However, the Miller et al. device as tested suffered from problems related to focusing the electron beam on the target, insufficient output and target design.

U.S. Pat. No. 5,471,516 (to Nunan), and assigned to Varian Associates, Inc., teaches a radiotherapy apparatus equipped with a low dosage localizing and portal imaging x-ray source. The device disclosed in the Nunan patent incorporates an x-ray source inside the treatment head of an accelerator to achieve positioning of a low energy x-ray source coincident with a high energy x-ray source.

Portal films or electronic portal imaging systems are used to verify tumor positioning. Megavolt therapeutic x-rays emerging from the patient are used to generate the images. Unfortunately, the images are of inherently low contrast and poor quality.

The patent to Fenn (U.S. Pat. No. 5,737,384) discloses an x-ray needle providing heating with microwave energy. Both the Fenn and Miller et al. patents are intended to be used interstitially to deliver radiation and heat to treat tumors and were not intended for imaging purposes.

The Nunan patent is mainly concerned with the retractable target, and, in particular, as it relates to the application of low energy x-rays. The apparatus set forth in the Nunan patent does not provide adequate focusing which causes decreased output and creates stray sources of x-rays in the head. Additionally, the Nunan apparatus locates the entire generating device inside the head of the machine, and it is not capable of variable energies. In order to achieve optimum diagnostic images, it is essential to have control over the electron energies being used to generate the x-ray beam.

SUMMARY OF THE INVENTION

The foregoing and other deficiencies of the prior art are addressed by the present invention which is directed to an apparatus for taking high quality images of radiotherapy treatments to confirm the accuracy of those treatments.

The present invention can be employed by modifying existing target mechanisms used in the treatment heads of linear accelerators. The electron drift tube is made long enough to penetrate the substantial shielding of a linear accelerator, thereby obviating the need to locate the entire generating device within the head of the machine. The diameter of the drift tube of the present invention is made small enough to penetrate the shielding without causing undue leakage of radiation.

An object of the present invention is to generate a diagnostic energy x-ray beam with variable energy.

Another object of the present invention is to provide an apparatus for taking high quality images of radiotherapy treatments having compact size with very thin electron guide and small target.

Yet another object of the present invention is to provide an apparatus for taking high quality images of radiotherapy treatments to verify those treatments.

Still another object of the present invention is to provide an apparatus and method for taking high quality images of radiotherapy treatments at lower energies and of higher quality than currently available.

Another object of the present invention is to provide an apparatus for taking high quality images of radiotherapy treatments where the diagnostic x-ray needle can fit into the treatment head of medical linear accelerators.

BRIEF DESCRIPTION OF THE DRAWINGS

The foregoing and other attributes and objects of the present invention will be described with respect to the following drawings in which.

DETAILED DESCRIPTION OF THE INVENTION

Figure 3:
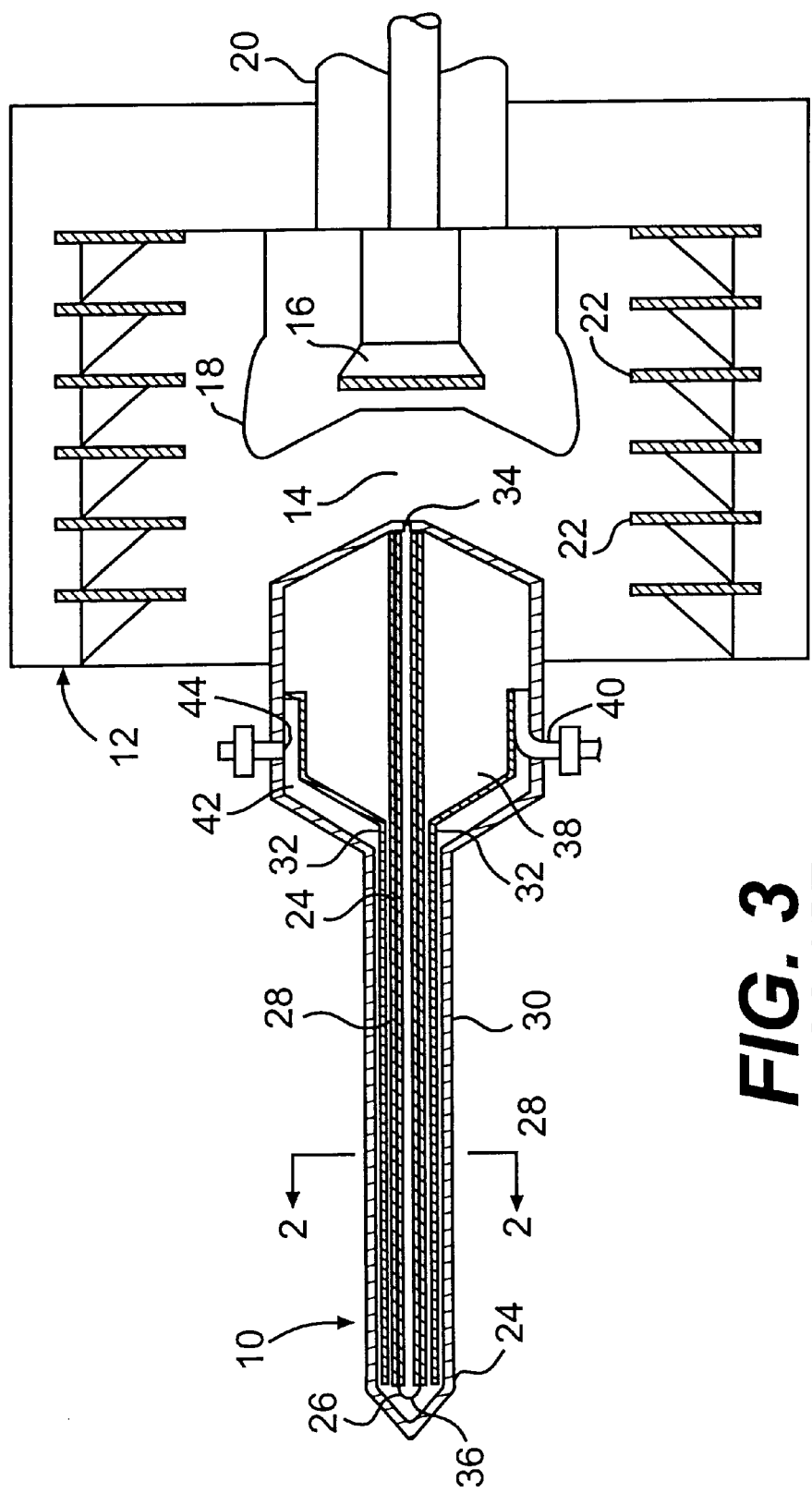
FIG. 3 is a diagram of an x-ray apparatus as taught in U.S. Pat. No. 5,165,093 which has an interstitial needle.

Referring to FIG. 3, a conventional x-ray apparatus having an interstitial x-ray needle is illustrated. The apparatus includes an x-ray needle 10 which is received in diode housing 12. The diode housing 12 includes a vacuum chamber 14, having an electron emitter 16 and a grid 18 disposed therein. The electron emitter 16 is connected to a high voltage source.

The x-ray needle 10 is made up of an elongated x-ray tube 24, a converter element 26, a solenoid coil 28, an elongated outer casing 30, and a pipe 32. An open end 34 of the x-ray tube 24 is connected to the vacuum chamber 14, and the converter element 26 is located at the tip of the opposite end of the x-ray tube 24 so that electrons emitted by the electron emitter 16 will be converted into x-rays. The emitted electrons are confined by a magnetic field generated by the solenoid coil 28, wound around the x-ray tube 24. The x-ray tube 24 and the solenoid coil 28 are enclosed in the outer casing 30. The pipe 32 is positioned between the outer casing 30 and the x-ray tube 24 to create an inner annular flow channel 38. The flow channel 38 extends between the tip 36 of the x-ray tube 24, from a coolant inlet 40 in the casing 30 through an outer annular flow chamber 42 to a coolant outlet 44, in disposed in the outer casing 30.

Figure 1:
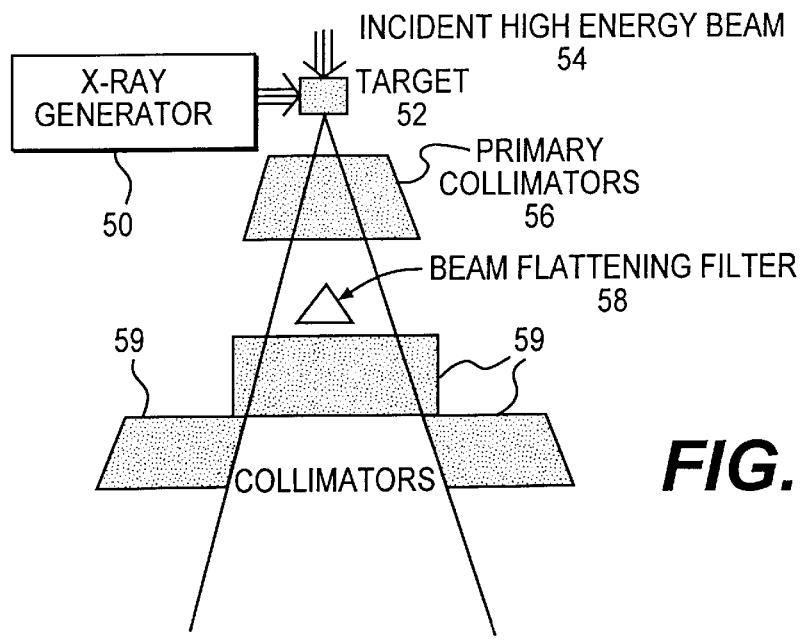
FIG. 1 is a schematic view of a low energy x-ray needle shifting into a energy target location according to the present invention.
Figure 2:
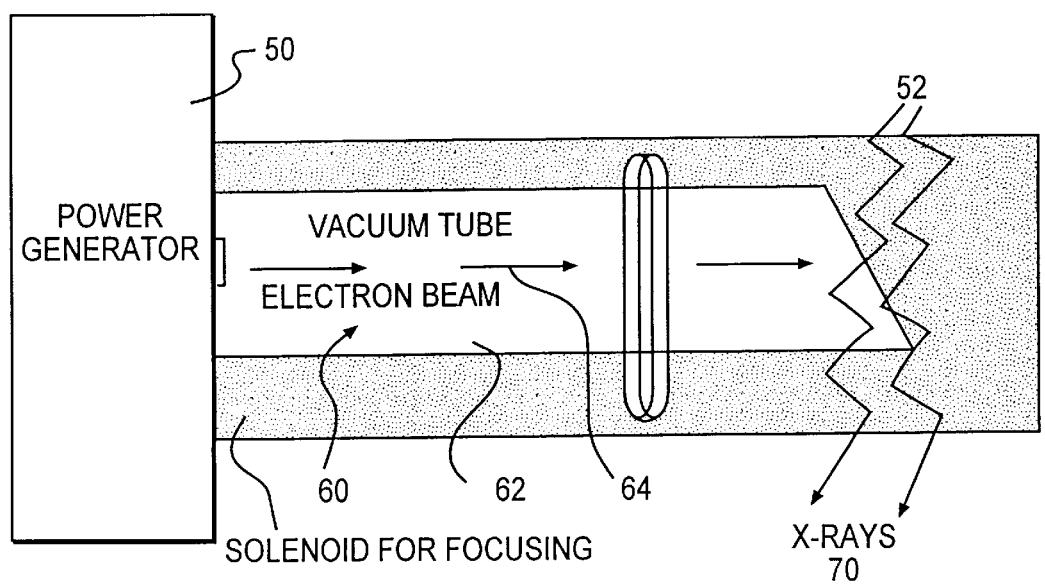
FIG. 2 is a schematic view of a low energy x-ray needle having a diameter of approximately 1 cm according to the present invention.

The present invention as shown in FIGS. 1 and 2, focuses the electron beam so that the device can be used for diagnostic imaging. The apparatus of the present invention combines an electron gun and drift tube to produces superior focusing capabilities.

A typical x-ray generator 50 is used. With the x-ray needle device 10, the drift tube 60 can be made long enough to penetrate the substantial shielding of a medical linear accelerator, thereby eliminating the need to locate the entire device within the head of the device (see the Nunan patent U.S. Pat. No. 5,471,516). The diameter of the drift tube 60 is small enough to penetrate the shielding without causing undesired radiation leakage problems.

High energy beams, such as those used to treat a patient have inherently less radiographic contrast than low energy x-rays. This results because of different x-ray interactions at low energies, namely the photoelectric effect, than the high energy interactions, caused by the Compton effect. As a consequence, images taken with high energy beams can not have much radiographic contrast as low energy beams. For this reason, conventional diagnostic x-rays are taken at lower energies.

The apparatus of the present invention produces much better images than current conventional devices, fits inside a conventional linear accelerator head, and can deliver variable energy. The operating parameters are similar to the parameters for conventional diagnostic x-ray units with adaption for fitting the apparatus within a medical linear accelerator head. The electron beam has an energy of 60 to 120 KeV. The target material is preferably tungsten due to its heat capacity and high atomic number electron beam current, between 10 to 200 mA. A maximum exposure time is one second, thereby requiring currents up to 200 mA. A drift tube diameter of approximately one centimeter could be employed.

Referring to FIG. 1 the x-ray generator 50 emits x-rays to target 52, preferably made from tungsten, which also receives an incident high energy beam 54. Primary collimators 56, a beam flattening filter 58 and secondary collimators 59 are employed to focus the energy beam. The low energy x-ray needle 10 is shifted into the high energy at the target location to obtain diagnostic images.

The x-ray generator 50, is shown in FIG. 2, in which a low energy x-ray needle 10 is employed having a drift tube 60. The drift tube 60 includes the vacuum tube 62, and the electron beam 64 from the x-ray generator 50 travels through the drift tube 60 to strike the target 52 and produce x-rays 70. By varying the electron beam energy between 60 and 120 KeV, optimal diagnostic images can be obtained.

As a result of the foregoing configuration, the apparatus has a compact size with a very thin electron guide and small target. The present invention can take images at lower energies and thereby produce higher quality images. The diagnostic x-ray needle of the present invention can fit inside the treatment head of a medical line accelerator.

Having described several embodiments of the apparatus for taking high quality images of radiotherapy treatments to confirm the accuracy of those treatments in accordance with the present invention, it is believed that other modifications, variations and changes will be suggested to those skilled in the art in view of the description set forth above. It is therefor to be understood that all such variations, modifications and changes are believed to fall within the scope of the invention as defined in the appended claims.

What is claimed is:

1. An apparatus using an X-ray source for radiation therapy port verification comprising:

a linear accelerator for producing an electron beam;

an elongated electron drift tube extending through shielding surrounding said linear accelerator, said drift tube having a relatively small diameter;

a target receiving said electron beam, and producing an x-ray beam; and primary and secondary collimators and a beam flattening filter for focusing said x-ray beam, wherein energy of said x-ray beam can be varied to achieve a desired radiographic contrast.

2. An apparatus as claimed 1, wherein said energy of said x-ray beam is between 60–120 KeV.

3. An apparatus as claimed in claim 1, wherein said target is made of tungsten.

4. An apparatus as claimed in claim 1, wherein said drift tube has a maximum diameter of approximately 1 centimeter.

5. An apparatus as claimed in claim 1, wherein said target is disposed in a treatment head of said linear accelerator, where respective focal spots of said target and linear accelerator can be made coincident.

6. An apparatus using an x-ray source for radiation therapy port verification comprising:

a linear accelerator for producing an electron beam;

an elongated electron drift tube having a diameter of approximately no greater than 1 centimeter, extending through shielding surrounding said linear accelerator;

a target receiving said electron beam and producing an x-ray beam, and primary and secondary collimators and a beam flattening filter for focusing said x-ray beam, wherein energy of said x-ray beam can be between 60–120 KeV to achieve a desired radiographic contrast, said x-ray beam being shifted into high energy to obtain diagnostic images after port verification, said x-ray beam being produced in a head of said linear accelerator.

* * * * *